US012653577B2

(12) United States Patent
Prior et al.

(10) Patent No.: US 12,653,577 B2
(45) Date of Patent: Jun. 16, 2026

(54) ROBOTIC UTERINE MANIPULATORS WITH ROLLABLE SLEEVES

(71) Applicant: Covidien LP, Mansfield, MA (US)

(72) Inventors: Scott J. Prior, Branford, CT (US); Arvind Rajagopalan Mohan, Dracut, MA (US); Nikolai D. Begg, Wellesley, MA (US); Kevin R. Slisz, St. Augustine, FL (US); Zachary Traina, Verona, NJ (US)

(73) Assignee: Covidien LP, Mansfield, MA (US)

( * ) Notice: Subject to any disclaimer, the term of this patent is extended or adjusted under 35 U.S.C. 154(b) by 278 days.

(21) Appl. No.: 18/218,481

(22) Filed: Jul. 5, 2023

(65) Prior Publication Data

US 2023/0346429 A1      Nov. 2, 2023

Related U.S. Application Data

(63) Continuation of application No. 17/318,504, filed on May 12, 2021, now Pat. No. 11,730,517.

(60) Provisional application No. 63/023,390, filed on May 12, 2020.

(51) Int. Cl.
| | |
|---|---|
| *A61B 17/42* | (2006.01) |
| *A61B 17/00* | (2006.01) |
| *A61B 34/00* | (2016.01) |
| *A61B 34/30* | (2016.01) |
| *A61B 34/35* | (2016.01) |

(52) U.S. Cl.
CPC .... *A61B 17/4241* (2013.01); *A61B 17/00234* (2013.01); *A61B 34/35* (2016.02); *A61B 34/70* (2016.02); *A61B 2017/00238* (2013.01); *A61B 2034/301* (2016.02)

(58) Field of Classification Search
CPC ................ A61B 17/42; A61B 17/4241; A61B 2017/00336; A61B 2017/4216; A61B 2017/4225; A61B 2017/4233; A61B 2018/00559
See application file for complete search history.

(56) References Cited

U.S. PATENT DOCUMENTS

| | | | |
|---|---|---|---|
| 4,775,362 | A | 10/1988 | Kronner |
| 5,104,377 | A | 4/1992 | Levine |
| 5,403,342 | A | 4/1995 | Tovey et al. |
| 5,562,679 | A | 10/1996 | Valtchev |
| 5,840,077 | A | 11/1998 | Rowden et al. |
| 6,235,037 | B1 | 5/2001 | East et al. |
| 8,128,622 | B2 | 3/2012 | Podhajsky et al. |
| 8,460,289 | B2 | 6/2013 | Sartor |
| 8,702,723 | B2 | 4/2014 | Walter |
| 8,784,410 | B2 | 7/2014 | Dunning |
| 8,828,023 | B2 | 9/2014 | Neff et al. |
| 9,554,827 | B2 | 1/2017 | Omori |
| 9,687,275 | B1 | 6/2017 | Fenton et al. |
| 10,258,359 | B2 | 4/2019 | Kapadia |

(Continued)

FOREIGN PATENT DOCUMENTS

WO      2016025132 A1      2/2016

*Primary Examiner* — Martin T Ton

(74) *Attorney, Agent, or Firm* — Carter, DeLuca & Farrell LLP

(57) ABSTRACT

A uterine manipulator includes an elongated shaft, a colpotomy cup supported on the elongated shaft, a distal shaft extending distally from the colpotomy cup to a distal tip, and a rollable sleeve supported on the distal tip.

12 Claims, 8 Drawing Sheets

(56)     References Cited

U.S. PATENT DOCUMENTS

| 11,730,517 | B2 | 8/2023 | Prior et al. | |
| 2002/0082634 | A1 | 6/2002 | Kammerer et al. | |
| 2006/0258909 | A1* | 11/2006 | Saadat .................. | A61B 46/10 |
| | | | | 600/121 |
| 2008/0215031 | A1 | 9/2008 | Belfort et al. | |
| 2010/0305578 | A1* | 12/2010 | Auerbach .......... | A61B 17/4241 |
| | | | | 606/119 |
| 2010/0331859 | A1 | 12/2010 | Omori | |
| 2012/0016185 | A1 | 1/2012 | Sherts et al. | |
| 2014/0142719 | A1* | 5/2014 | Gittard .................. | A61F 2/958 |
| | | | | 623/23.65 |
| 2014/0243843 | A1 | 8/2014 | Havel et al. | |
| 2015/0133737 | A1* | 5/2015 | Bacich ............... | A61B 17/1204 |
| | | | | 600/207 |
| 2016/0000464 | A1* | 1/2016 | Coomarasamy ... | A61B 17/1204 |
| | | | | 606/193 |
| 2017/0112535 | A1* | 4/2017 | Ahluwalia ......... | A61B 17/4241 |
| 2017/0281231 | A1 | 10/2017 | Langell et al. | |
| 2017/0325844 | A1* | 11/2017 | Prior .................. | A61B 1/00082 |
| 2018/0214144 | A1 | 8/2018 | Fischvogt et al. | |
| 2018/0325554 | A1 | 11/2018 | Prior et al. | |
| 2019/0223912 | A1* | 7/2019 | Einarsson .......... | A61B 18/1485 |
| 2022/0151678 | A1 | 5/2022 | Kapadia | |
| 2022/0192707 | A1* | 6/2022 | Barakat .................. | A61B 34/30 |

* cited by examiner

122a

122

122a

"B"

"A"

"A"

122

ROBOTIC UTERINE MANIPULATORS WITH ROLLABLE SLEEVES

CROSS REFERENCE TO RELATED APPLICATIONS

This application is a continuation of U.S. patent application Ser. No. 17/318,504, filed May 12, 2021, which claims the benefit of U.S. Provisional Application Ser. No. 63/023, 390, filed May 12, 2020, the entire contents of each of which are incorporated by reference herein.

TECHNICAL FIELD

This disclosure relates to hysterectomy and, more particularly, to robotic uterine manipulators.

BACKGROUND

Colpotomy, one of the final steps in a hysterectomy, requires making a circular incision in vaginal tissue to separate the uterus from the vagina with a cutting tool such as an electrosurgical instrument. This incision is typically performed with the aid of a uterine manipulator. Uterine manipulators are conventionally used during laparoscopic hysterectomy procedures to position the vagina and the cervix to facilitate separation and to enable removal of the uterus or other tissue specimens subsequent to performance of a colpotomy.

SUMMARY

In accordance with an aspect of this disclosure, a uterine manipulator includes an elongated shaft, a colpotomy cup supported on the elongated shaft, a distal shaft, and a rollable sleeve. The distal shaft extends distally from the colpotomy cup to a distal tip. The rollable sleeve is supported on the distal tip.

In aspects, the rollable sleeve may include a body having a closed distal end portion supported on the distal tip of the distal shaft, and a movable proximal end portion extending proximally from the closed distal end portion. The movable proximal portion may be movable in a proximal direction relative to the closed distal end portion to elongate the rollable sleeve. The movable proximal portion may uncoil as the movable proximal portion moves in a proximal direction relative to the closed distal portion. The closed distal portion may elongate as the movable proximal portion uncoils.

In aspects, the rollable sleeve may be movable from a first position in which the rollable sleeve has a first length and a second position in which the rollable sleeve has a second length. The second length may be longer than the first length.

In aspects, the rollable sleeve may include a polymeric material. The rollable sleeve may be sufficiently elastic to expand away from the distal shaft when the rollable sleeve receives inflation fluid within a pocket defined by an inner surface of rollable sleeve.

In aspects, the rollable sleeve includes an inflatable balloon.

According to another aspect, a uterine manipulator system includes a fluid source and a uterine manipulator. The uterine manipulator is coupled to the fluid source. The uterine manipulator includes an elongated shaft, a colpotomy cup supported on the elongated shaft, a distal shaft extending distally from the colpotomy cup to a distal tip, and a rollable sleeve supported on the distal tip. The rollable sleeve is in fluid communication with the fluid source.

In aspects, the rollable sleeve may be sufficiently elastic to expand away from the distal shaft when the rollable sleeve receives inflation fluid from the fluid source.

According to still another aspect, a robotic uterine manipulator system includes a robotic arm and a uterine manipulator supported on the robotic arm. The uterine manipulator includes an elongated shaft, a colpotomy cup supported on the elongated shaft, a distal shaft extending distally from the colpotomy cup to a distal tip, and a rollable sleeve supported on the distal tip.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, serve to explain the principles of this disclosure, wherein.

DETAILED DESCRIPTION

Figure 1:
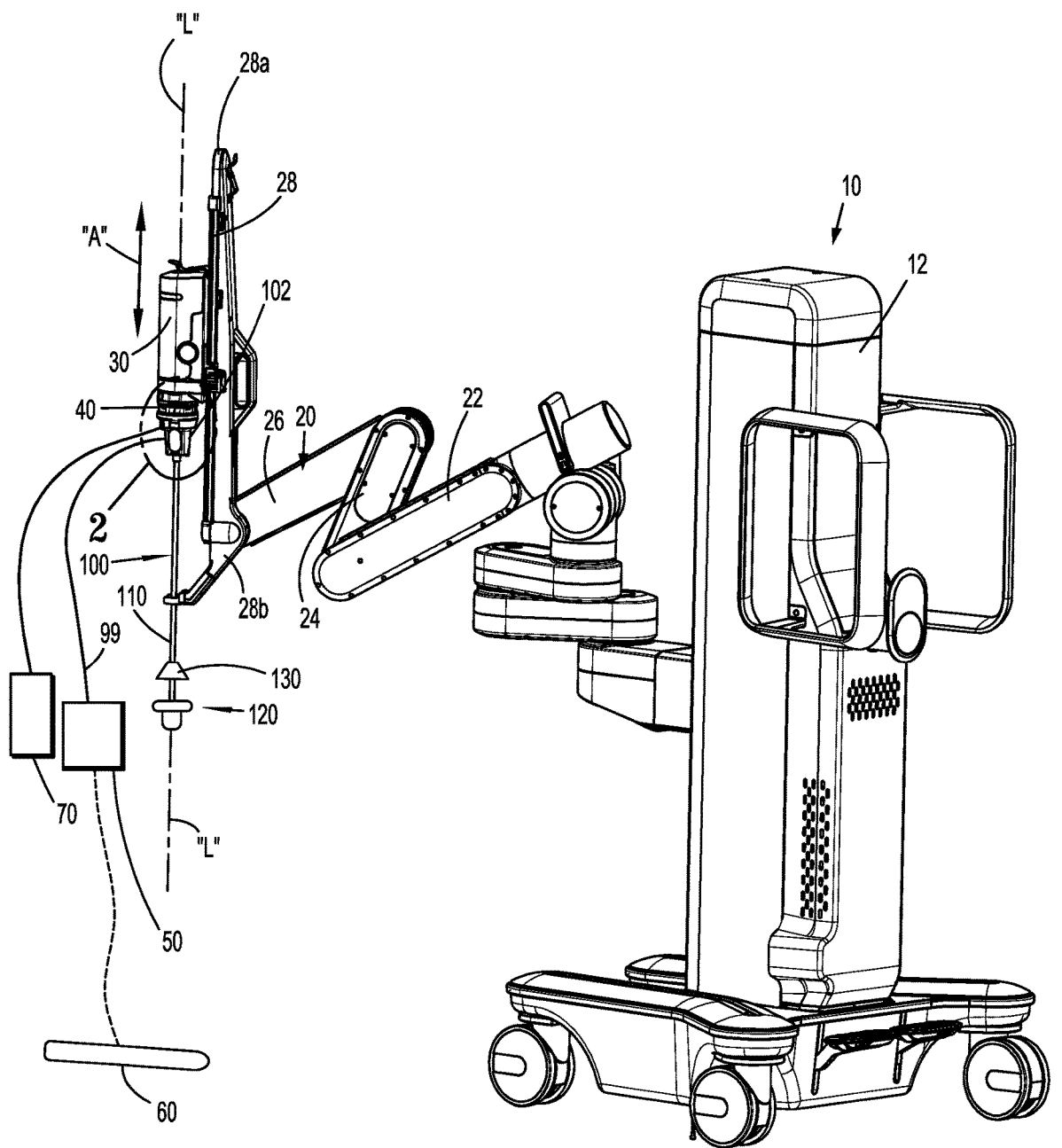
FIG. 1 is a perspective view of a robotic system in accordance with the principles of this disclosure.

Aspects of this disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Robotic surgical systems have been used in minimally invasive medical procedures and can include robotic arm assemblies. Such procedures may be referred to as what is commonly referred to as "Telesurgery." Some robotic arm assemblies include one or more robot arms to which surgical instruments can be coupled. Such surgical instruments include, for example, electrosurgical forceps, cutting instruments, staplers, graspers, electrocautery devices, or any other endoscopic or open surgical devices. Prior to or during use of the robotic surgical system, various surgical instruments can be selected and connected to the robot arms for selectively actuating end effectors of the connected surgical instruments. Some of these surgical instruments utilize electrical energy, for example, to effectuate electrocautery.

Figure 2:
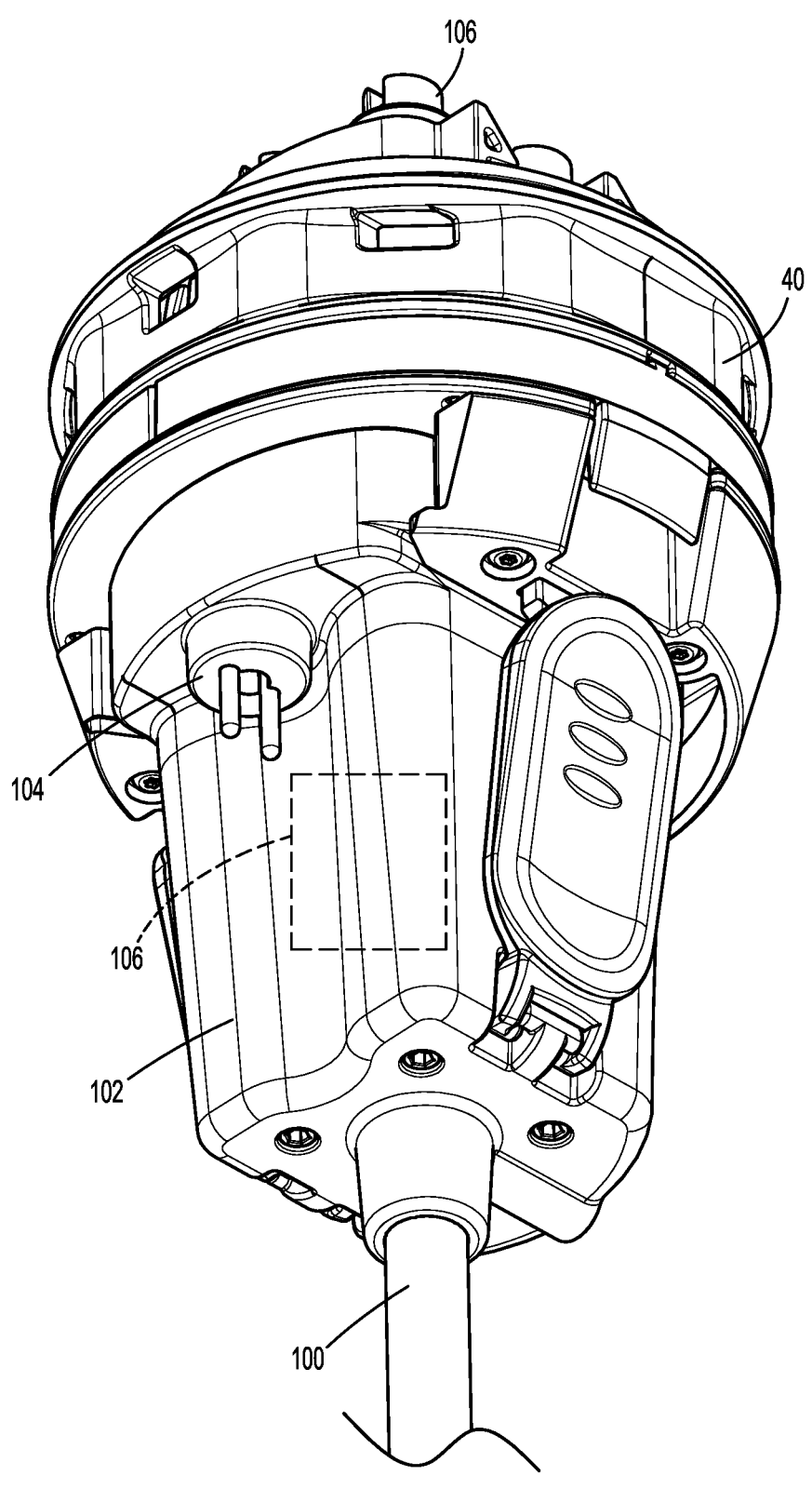
FIG. 2 is an enlarged, perspective view of a proximal portion of a robotic uterine manipulator of the robotic colpotomy system of FIG. 1.

With reference to FIGS. 1 and 2, a robotic surgical system, such as the robotic colpotomy system 10 illustrated in FIG. 1, includes a robotic arm assembly 20 that supports a surgical instrument, such as a uterine manipulator 100, for effectuating a surgical procedure (e.g., a colpotomy), an instrument drive unit ("IDU") 30 that imparts driving force to uterine manipulator 100, and a sterile interface module 40 that enables a proximal housing assembly 102 of uterine manipulator 100 to interface with IDU 30. This interface advantageously maintains sterility, provides a means to transmit electrical communication between robotic colpotomy system 10 and uterine manipulator 100, provides a means for transferring torque (e.g., rotational force) from robotic colpotomy system 10 (e.g., IDU 30) to uterine manipulator 100 for performing a function (e.g., sealing, cutting, manipulating, etc.) with uterine manipulator 100 and/or provides a means to selectively attach/remove uterine manipulator 100 to robotic colpotomy system 10 (e.g., for rapid instrument exchange). For a more detailed description of similar sterile interface modules and components thereof, reference can be made to WO2017205308 by Zemlock et al., the entire contents of which are incorporated by reference herein.

Robotic colpotomy system 10 further includes an energy source such as an electrosurgical generator 50 that couples to uterine manipulator 100 and/or any number of other surgical instruments such as an electrosurgical probe or an electrocautery blade 60 via an electrosurgical cable 99 and a connector assembly 104 supported by sterile interface module 40 and/or proximal housing assembly 102 of uterine manipulator 100. For a more detailed description of one example of an electrosurgical generator, reference can be made to U.S. Pat. No. 8,784,410, the entire contents of which are incorporated by reference herein. For a more detailed description of one example of connector assembly 104, reference can be made to U.S. Patent Application No. 62/823,036, filed Mar. 25, 2019, and entitled "Robotic Surgical Systems with Electrical Switch of Instrument Attachment," the entire contents of which are incorporated by reference herein. For a more detailed description of one example of an electrocautery blade 60, reference can be made to U.S. Pat. No. 8,128,622 or U.S. Pat. No. 8,460,289, the entire contents of each of which are incorporated herein by reference.

Robotic colpotomy system 10 employs various robotic elements to assist the clinician and allow remote operation (or partial remote operation) of surgical instrumentation such as uterine manipulator 100. Various robotic arms, gears, cams, pulleys, electric and mechanical motors, etc. may be employed for this purpose and may be designed with robotic colpotomy system 10 to assist the clinician during the course of an operation or treatment, and which can be included with, and/or part of one or more drive mechanisms 106 of uterine manipulator 100, sterile interface module 40, and/or instrument drive unit 30. Such robotic systems may include remotely steerable systems, automatically flexible surgical systems, remotely flexible surgical systems, remotely articulating surgical systems, wireless surgical systems, modular or selectively configurable remotely operated surgical systems, etc.

Robotic colpotomy system 10 includes a medical work station (not shown) that may be employed with one or more consoles positioned next to the operating theater or located in a remote location. In this instance, one team of clinicians may prep the patient for surgery and configure robotic colpotomy system 10 with uterine manipulator 100 while another clinician (or group of clinicians) remotely controls uterine manipulator 100 via the one or more consoles. As can be appreciated, a highly skilled clinician may perform multiple operations in multiple locations without leaving his/her remote console. This can be economically advantageous and a benefit to the patient or a series of patients. For a detailed description of exemplary medical work stations and/or components thereof, reference may be made to U.S. Pat. No. 8,828,023 and PCT Application Publication No. WO2016/025132, the entire contents of each of which are incorporated by reference herein.

With continued reference to FIG. 1, robotic arm assembly 20 of robotic surgical system 10 includes a cart 12 having robotic arms 22, 24, 26 that are pivotally coupled together and movable together and/or relative to one another and cart 12. Robotic arm 26 is coupled to a slide rail 28 that supports IDU 30 and sterile interface module 40 for operating uterine manipulator 100. IDU 30 defines a longitudinal axis "L" and is slidably supported on slide rail 28 and selectively axially movable along longitudinal axis "L," as indicated by arrows "A," between a proximal position adjacent a proximal end portion 28a of slide rail 28, and a distal position adjacent a distal end portion 28b of slide rail 28.

Robotic surgical system 10 can be in the form of an electrosurgical colpotomy system. In general, components of the electrosurgical colpotomy system can be used to effectuate a colpotomy. Briefly, when using a uterine manipulator for colpotomy during a laparoscopic hysterectomy, a colpotomy cup can be used as a backstop for a clinician to circumferentially cut along with a laparoscopic tool (e.g., radiofrequency or "RF" tool) around the uterus.

With reference now to FIGS. 1-4C, uterine manipulator 100 includes an elongated shaft assembly 110 that extends from proximal housing assembly 102 to a distal colpotomy assembly 120. Distal colpotomy assembly 120 includes a colpotomy cup 130 and a distal shaft 122 that extends distally from colpotomy cup 130 to a distal tip 122a. Distal shaft 122 supports a rollable sleeve 124 on the distal tip 122a thereof. Rollable sleeve 124 may be in the form of an inflatable balloon. Rollable sleeve 124 includes a body 124a having a closed distal end portion 124b supported on the distal tip 122a of the distal shaft 122. Rollable sleeve 124 further includes a movable proximal end portion 124c extending proximally from the closed distal end portion 124b of body 124a and positioned to move relative to the closed distal end portion 124b between a coiled position (FIG. 4A) and an extended position (FIG. 4B). Movable proximal end portion 124c is configured to uncoil or unravel away from the closed distal end portion 124b to elongate rollable sleeve 124 and/or coil toward closed distal end portion 124b to shorten a length of rollable sleeve 124 (see, for example, FIGS. 4A-4B). In particular, movable proximal end portion 124c is configured to roll and/or unroll in a spiral fashion with any number of rings or coils concentrically arranged relative to one another). Rollable sleeve 124 has an inner surface that defines a pocket 124d for receiving distal shaft 122 or portions thereof (e.g., distal tip 122a) therein so that rollable sleeve 124 frictionally constricts onto distal shaft 122 for maintaining the rollable sleeve 124 secured to distal shaft 122 while in either the coiled or extended positions thereof.

Figures 3, 4A, 4B, 4C:
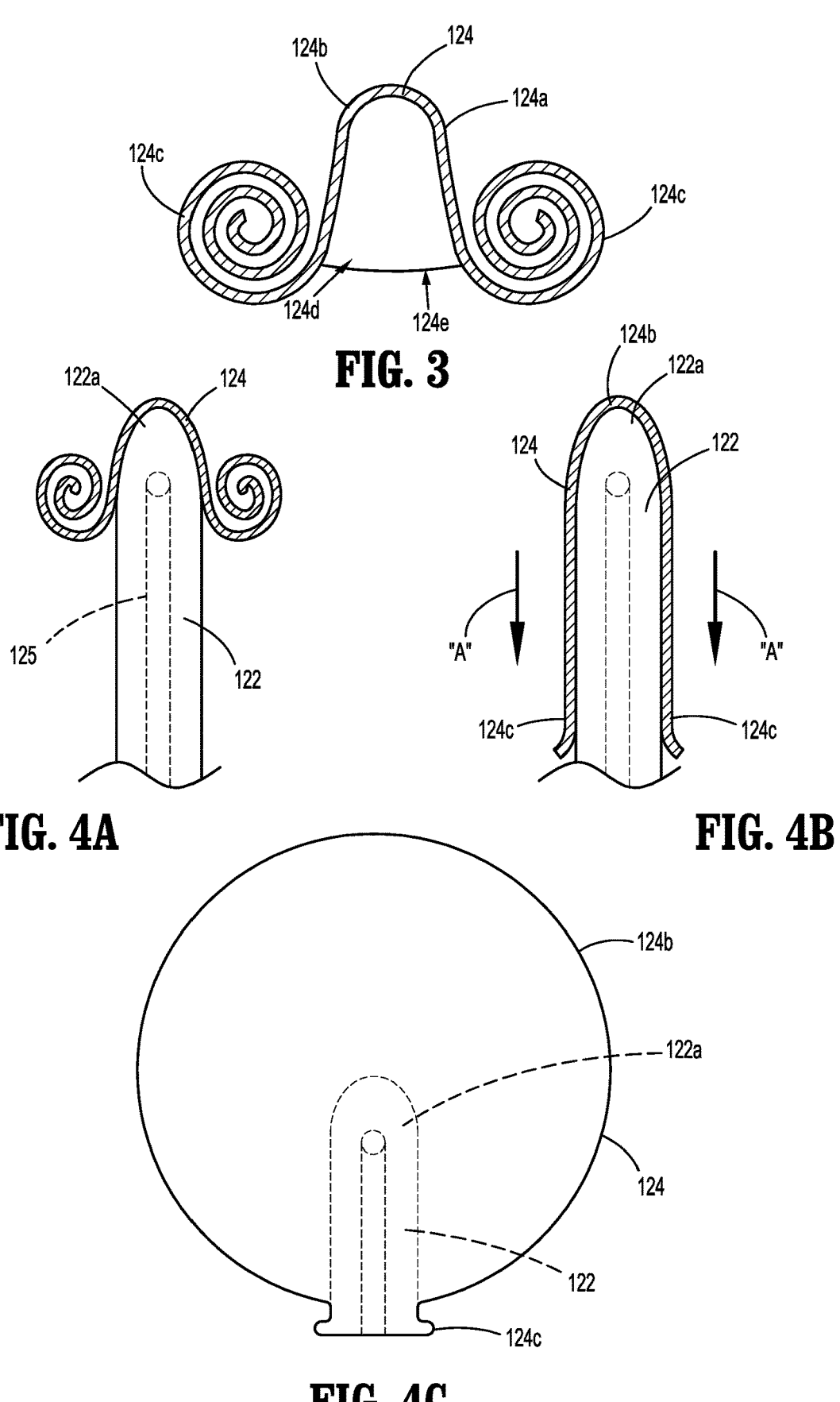
FIG. 3 is an enlarged, cross-sectional view of a rollable sleeve of the robotic uterine manipulator of FIG. 2.
FIGS. 4A-4C are progressive views of a distal portion of the robotic uterine manipulator which illustrate the rollable sleeve of FIG. 3 in various positions relative to a distal shaft of the robotic uterine manipulator.

Rollable sleeve 124 can be formed of any suitable elastic material that has sufficient elasticity to frictionally retain rollable sleeve 124 distal shaft 122 (e.g., on distal tip 122*a* thereof). Such material is also expandable relative to distal shaft 122, for instance, when inflation fluid "F" (e.g., saline; see FIG. 5D) is received within pocket 124*d* thereof. Rollable sleeve 124 is disposed in fluid communication with a fluid source 70 (e.g., saline) via a lumen 125 defined through distal shaft 122 for selectively inflating rollable sleeve 124 to move rollable sleeve 124 from an uninflated position (FIG. 4B) to an inflated position (FIG. 4C).

In aspects, rollable sleeve 124 can include any suitable polymeric material. For instance, such material can include an elastomeric material such as silicone rubber, polyurethane, polyester or the like. Rollable sleeve 124 may include any suitable biocompatible and/or biodegradable material. Rollable sleeve 124 can include one or more bioactive agents supported on, and/or retained within, one or more inner and/or outer surfaces of rollable sleeve 124. Such bioactive agents can be partially and/or wholly, impregnated, layered, and/or coated on and/or in one or more surfaces of rollable sleeve 124.

Figure 5A:
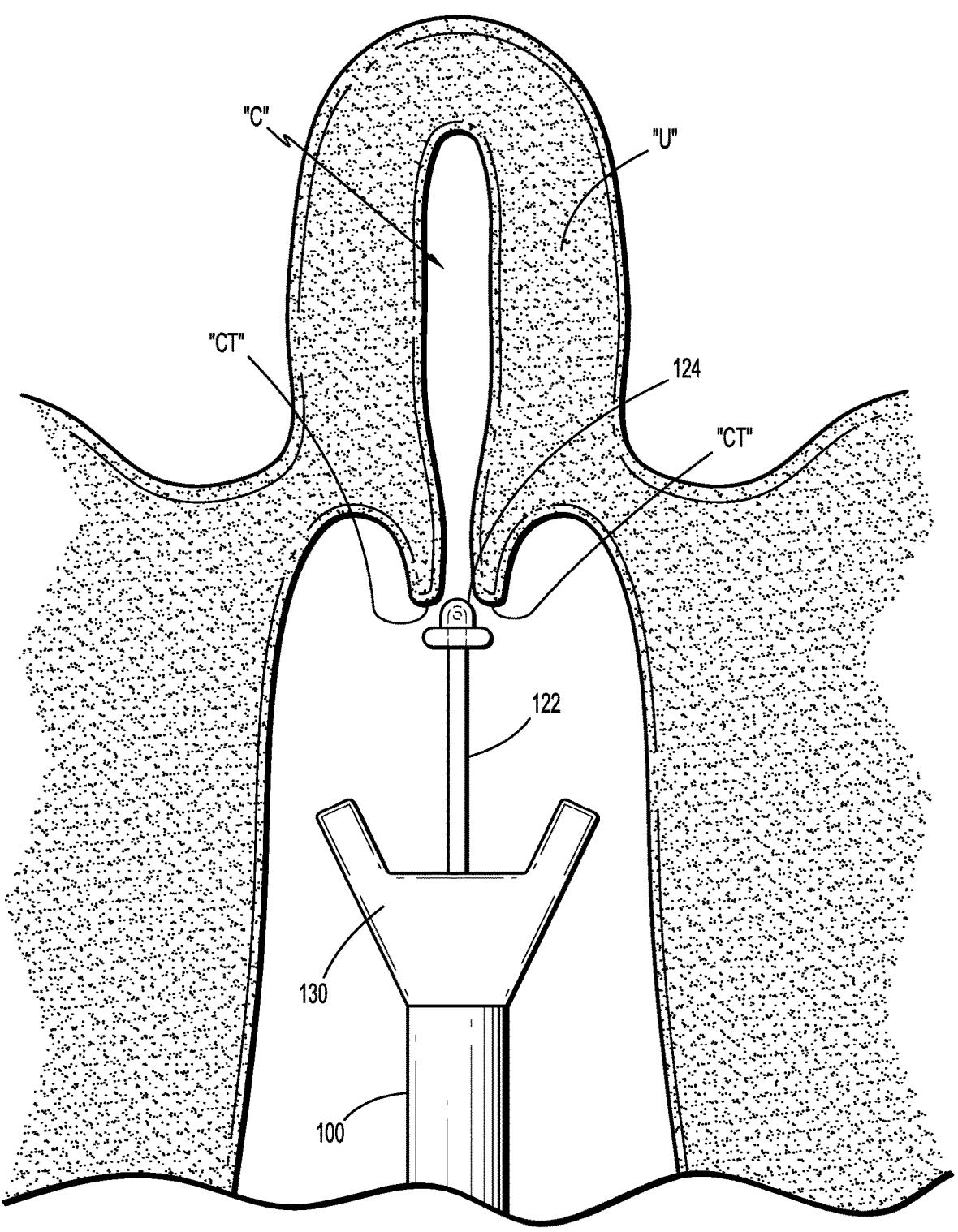
FIGS. 5A-5D are progressive views illustrating the robotic uterine manipulator being transvaginally inserted and the rollable sleeve thereof being introduced into a uterus.
Figure 5B:
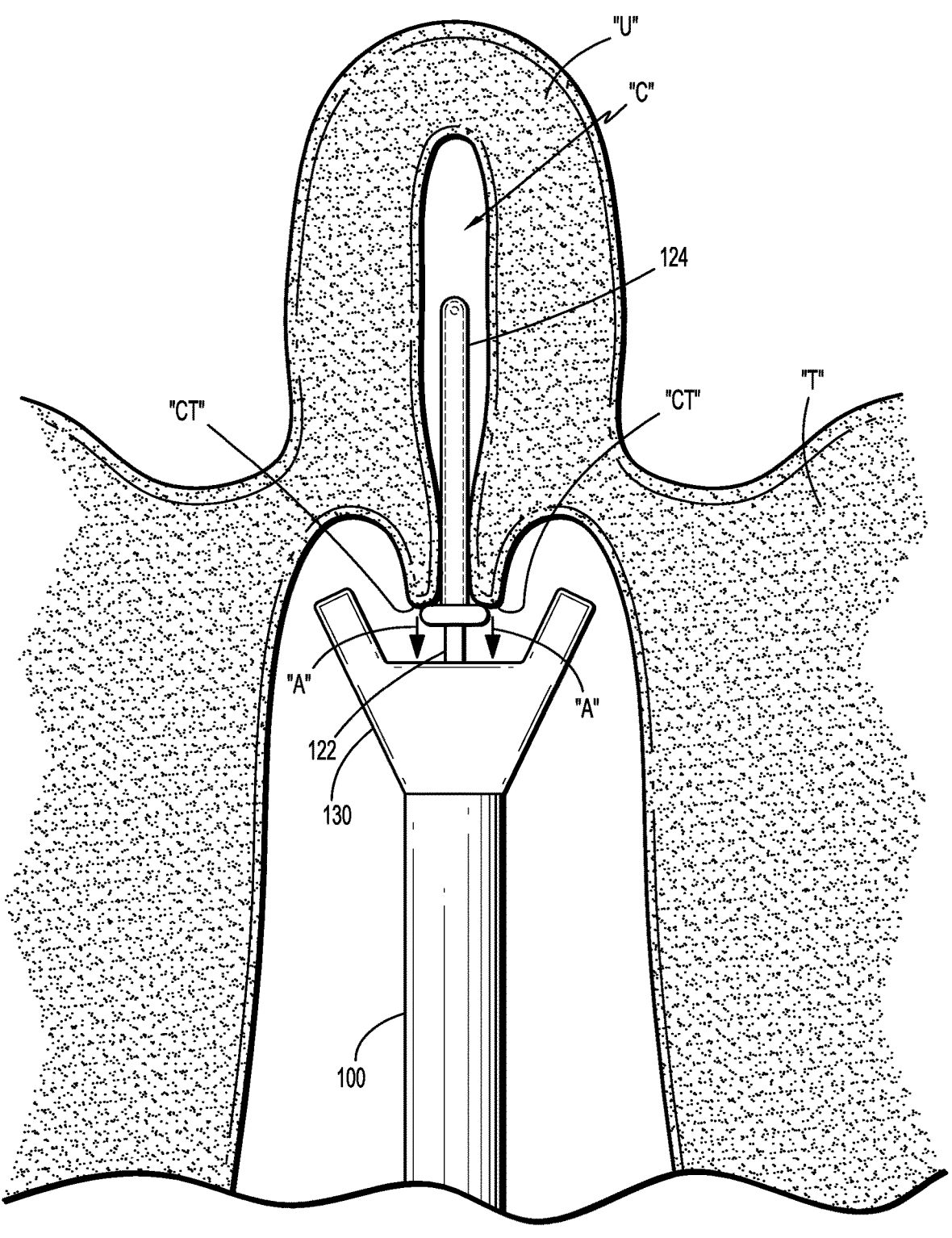
Figure 5C:
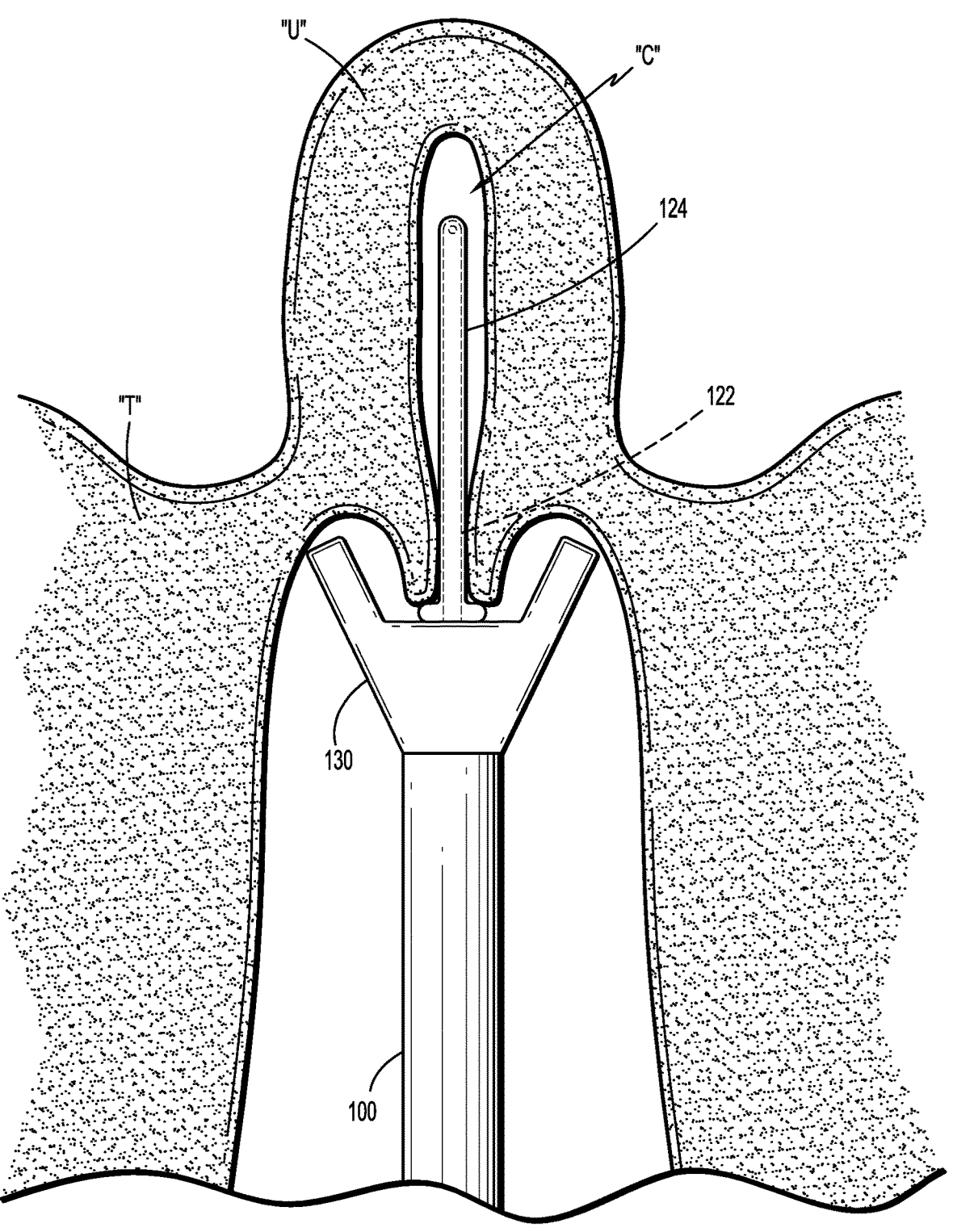
Figure 5D:
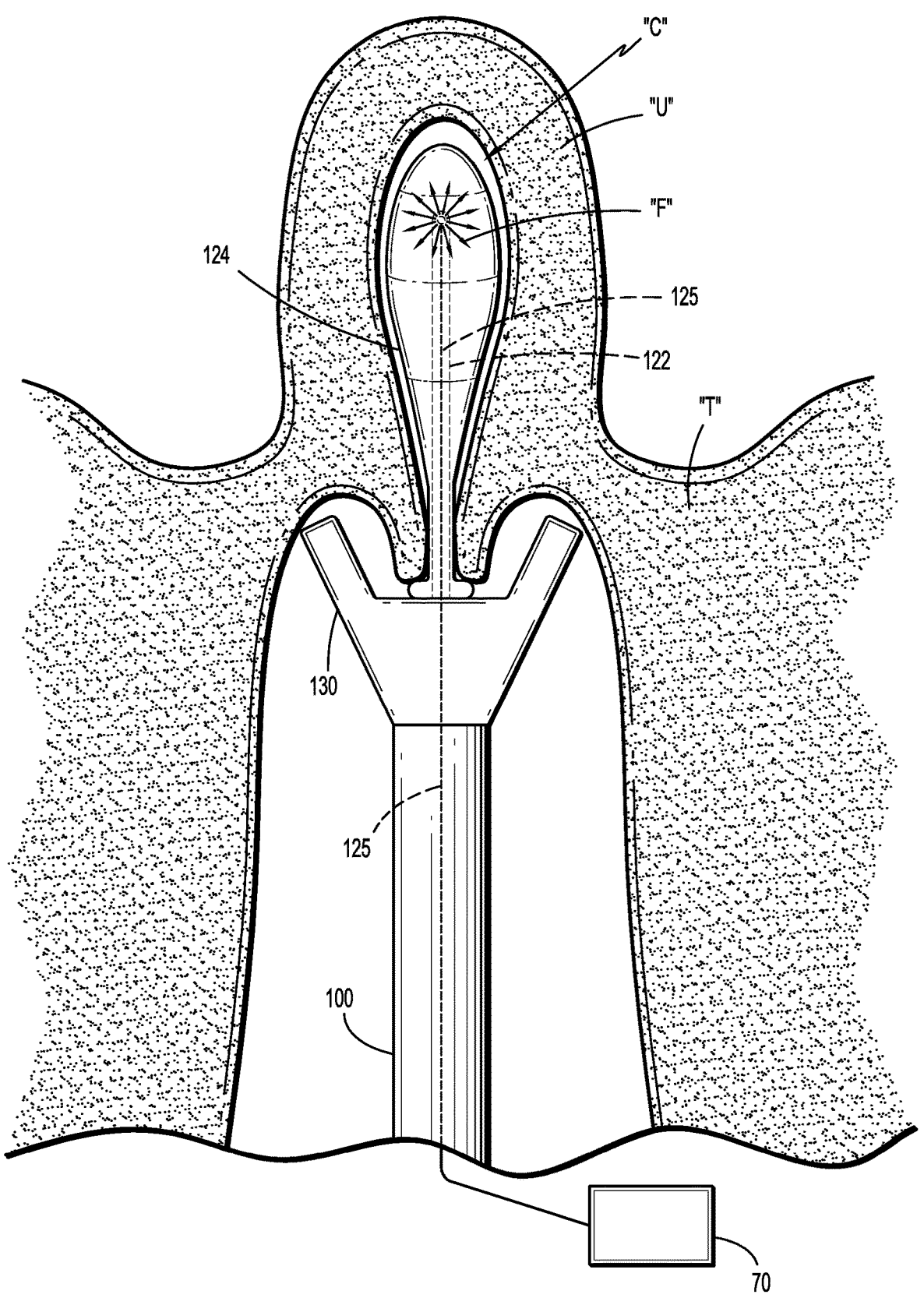

In use, as seen in FIGS. 5A-5D, distal tip 122*a* is configured to be inserted, for example, with rollable sleeve 124 secured thereto (e.g., frictionally retained thereon), into a cavity "C" of a patient's uterus "U" for inflating rollable sleeve 124 therein to secure distal colpotomy assembly 120 to the uterus "U" of the patient. As rollable sleeve 124 engages cervical tissue "CT," the cervical tissue "CT" will push the movable proximal end portion 124*c* in a proximal direction relative to the closed distal end portion 124*b*, as indicated by arrows "A," as uterine manipulator is advanced distally so to that movable proximal end portion 124*c* uncoils toward the extended position of rollable sleeve 124, lengthening rollable sleeve 124 along distal shaft 122. Once uterine manipulator 100 is disposed in a desired position, for example, where colpotomy cup 130 is engaged with the cervical tissue "CT" and distal shaft 122/rollable sleeve 124 are within the cavity "C" of the patient's uterus "U," inflation fluid "F" can be received within pocket 124*d* of rollable sleeve 124 to inflate rollable sleeve 124 in the cavity "C" and conform rollable sleeve 124 to cavity "C" to secure uterine manipulator 100 in position (FIG. 5D). Once uterine manipulator 100 is secured, a colpotomy procedure can be effectuated. The rollable sleeve 124 can then be deflated as desired, for instance, by withdrawing distal shaft 122 from the rollable sleeve 124 so that an open end 124*e* of rollable sleeve 124 becomes exposed, releasing inflation fluid "F." Rollable sleeve 124 can then be removed (e.g., via a grasping forceps—not shown) or left for biodegradation. Alternatively, inflation source 70 may include or be coupled to a vacuum source for withdrawing the inflation fluid "F" back through uterine manipulator 100 so that proximal retraction of uterine manipulator 100 with draw rollable sleeve 124 with uterine manipulator 100 once rollable sleeve 124 is deflated.

Figure 6A:
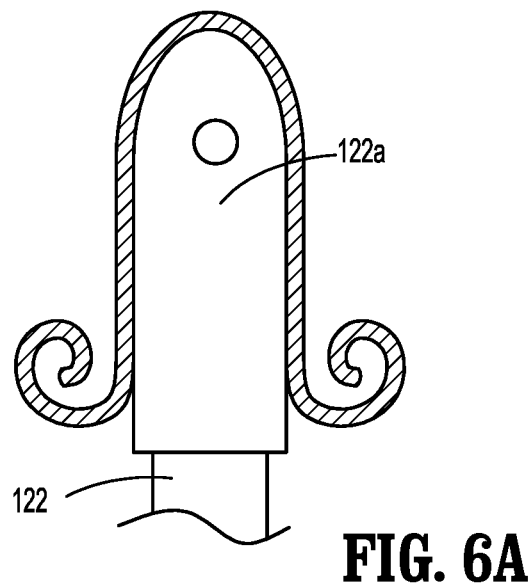
FIGS. 6A and 6B are progressive views of another robotic uterine manipulator having another distal shaft supporting the rollable sleeve of FIG. 3 and illustrating various positions of the rollable sleeve and distal shaft relative to one another.
Figure 6B:
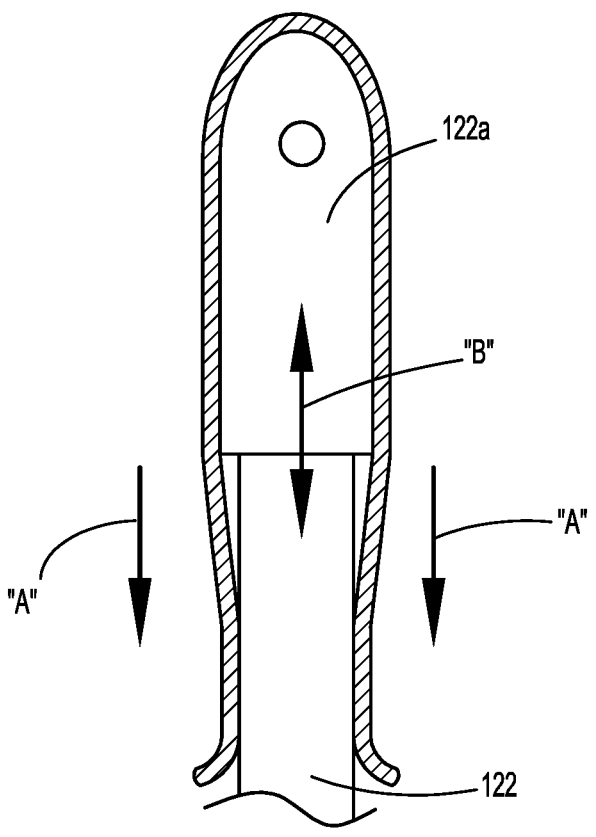

With reference to FIGS. 6A and 6B, in one aspect, distal tip 122*a* may be axially movable relative to distal shaft 122, as indicated by arrows "B," to selectively elongate distal shaft 122 and facilitate an extension and/or coiling of rollable sleeve 124 relative distal shaft 122, as indicated by arrows "A." For instance, distal tip 122*a* may be threadably coupled to distal shaft 122 and/or axially slidable relative to distal shaft 122 so that elongation may be effectuated via rotation and/or translation movement of distal tip 122*a* relative to distal shaft 122, where distal shaft 122 and/or distal tip 122*a* are operatively coupled to drive mechanism

106 via any suitable mechanical and/or electrical components for causing such rotational and/or translational movement.

Further, although detailed herein with respect to a robotic system, the disclosed uterine manipulators can be provided as manual and/or hand-held instruments. For a more detailed description of an exemplary hand-held uterine manipulator, reference can be made to U.S. Patent Application Publication No. 2018/0325554, the entire contents of which are incorporated by reference herein.

As used herein, the term "biodegradable" in reference to a material shall refer to the property of the material being able to be harmlessly absorbed by the body. In the present application, the terms "biodegradable," "bioresorbable," "bioerodable," and "bioabsorbable" are used interchangeably and are intended to mean the characteristic according to which a material decomposes, or loses structural integrity under body conditions (e.g., enzymatic degradation or hydrolysis) or are broken down (physically or chemically) under physiologic conditions in the body, such that the degradation products are excretable or absorbable by the body after a given period of time. The time period may vary, from about one hour to about several months or more, depending on the chemical nature of the material. In embodiments, the material may not be completely absorbed, provided the non-absorbed material poses no health risks and is biocompatible.

Further, the term "bioactive agent" includes "active therapeutic agent" (ATA) and can be used interchangeably. In its broadest sense, the term "bioactive agent" includes any substance or mixture of substances that have clinical use. The bioactive agents may invoke a biological action, exert a biological effect, or play a role in one or more biological processes. Consequently, bioactive agents may or may not have pharmacological activity per se, e.g., a dye, or fragrance. Alternatively, a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. The bioactive agent may be applied to the disclosed structure in any suitable form of matter, e.g., films, powders, liquids, gels and the like. The type and amount of bioactive agent(s) used will depend, among other factors, on the particular site and condition to be treated.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the disclosed sleeves and the surrounding tissues opposite the target tissue. In addition, anti-adhesive agents may be used to prevent adhesions from forming between the sleeves and packaging material thereof. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in a bioactive coating of this disclosure.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins, such as vitamin A, B-12, C, D, combinations thereof, and the like; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents also include biologics and protein therapeutics, such as, viruses, bacteria, lipids, amino acids, cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, α-IFN, and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Securement of any of the components of the disclosed devices may be effectuated using known securement techniques such welding, crimping, gluing, fastening, etc.

Persons skilled in the art will understand that the structures and methods specifically described herein and shown in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. A robotic uterine manipulator system comprising:
a robotic arm;
a fluid source; and
a uterine manipulator coupled to the robotic arm and the fluid source, the uterine manipulator including:
a colpotomy cup supported on an elongated shaft;
a distal shaft extending distally from the colpotomy cup to a distal tip; and
a sleeve covering a distal end of the distal tip, the sleeve in fluid communication with the fluid source and including a closed distal end portion supported on the distal tip of the distal shaft and a proximal end portion extending radially and proximally from the closed distal end portion, wherein the proximal end portion is rollable along the distal shaft relative to the closed distal end portion upon engagement of a radial portion of the proximal end portion with cervical tissue,
wherein the sleeve is movable from a first position in which the sleeve has a first length and a second position in which the sleeve has a second length, and
wherein the sleeve is elastic and configured to expand away from the distal shaft when the sleeve receives inflation fluid from the fluid source.

2. The robotic uterine manipulator system of claim 1, wherein the second length is longer than the first length.

3. The robotic uterine manipulator system of claim 1, wherein the proximal end portion is movable in a proximal direction relative to the distal end portion to elongate the sleeve.

4. The robotic uterine manipulator system of claim 1, wherein the sleeve is configured to coil and uncoil in response to relative movement between the distal end portion and the proximal end portion.

5. The robotic uterine manipulator system of claim 1, wherein the closed distal end portion elongates as the proximal end portion uncoils.

6. The robotic uterine manipulator system of claim 1, wherein the sleeve includes a polymeric material.

7. The robotic uterine manipulator system of claim 1, wherein the sleeve is frictionally constricted on the distal tip.

8. The robotic uterine manipulator system of claim 1, further comprising a drive mechanism operably coupled to the colpotomy cup.

9. The robotic uterine manipulator system of claim 1, wherein the sleeve includes an inflatable balloon.

10. The robotic uterine manipulator system of claim 1, wherein the sleeve is rollable and covers a distal end of the distal tip.

11. The robotic uterine manipulator system of claim 10, wherein the rollable sleeve includes a body having a closed distal end portion supported on the distal tip of the distal shaft.

12. The robotic uterine manipulator system of claim 11, wherein the body includes a proximal end portion extending radially and proximally from the closed distal end portion.

\* \* \* \* \*